United States Patent
DeBregeas et al.

(10) Patent No.: US 6,228,395 B1
(45) Date of Patent: May 8, 2001

(54) SUSTAINED-RELEASE MICROGRANULES CONTAINING DILTIAZEM AS THE ACTIVE PRINCIPLE

(75) Inventors: Patrice DeBregeas, Paris; Gérard LeDuc, Malesherbes; Pascal Oury, Paris; Pascal Suplie, Montaure, all of (FR)

(73) Assignee: Laboratoires des Produits Ethiques Ethypharm, Houdan (FR)

( * ) Notice: Subject to any disclaimer, the term of this patent is extended or adjusted under 35 U.S.C. 154(b) by 0 days.

(21) Appl. No.: 09/091,646

(22) PCT Filed: Dec. 23, 1996

(86) PCT No.: PCT/FR96/02040

§ 371 Date: Nov. 25, 1998

§ 102(e) Date: Nov. 25, 1998

(87) PCT Pub. No.: WO97/23219

PCT Pub. Date: Jul. 3, 1997

(30) Foreign Application Priority Data

Dec. 22, 1995 (FR) .................................................. 95 15361

(51) Int. Cl.⁷ ....................................................... A61K 9/58
(52) U.S. Cl. ........................ 424/458; 424/456; 424/457; 424/459; 424/497; 424/462; 514/772.3; 514/785
(58) Field of Search ..................................... 424/458, 461, 424/462, 490, 493, 494, 497, 456, 457, 495, 459

(56) References Cited

U.S. PATENT DOCUMENTS 5,834,024 * 11/1998 Heinicke et al. ..................... 424/497

FOREIGN PATENT DOCUMENTS

| 0 149 920 | 7/1985 | (EP) . |
| 0 263 083 | 4/1988 | (EP) . |
| 0 318 398 | 5/1989 | (EP) . |
| 0 322 277 | 6/1989 | (EP) . |
| WO 93/09767 | 5/1993 | (WO) . |

* cited by examiner

Primary Examiner—James M. Spear
(74) Attorney, Agent, or Firm—Foley & Lardner

(57) ABSTRACT

Novel forms of sustained-release microgranules (LP) containing diltiazem are disclosed. The microgranules consist of a neutral granular carrier coated with an active layer including diltiazem or a pharmaceutically acceptable salt thereof as the active principle, a surfactant and a binder, and an outer layer providing sustained release of the active principle (layer LP).

34 Claims, 1 Drawing Sheet

SUSTAINED-RELEASE MICROGRANULES CONTAINING DILTIAZEM AS THE ACTIVE PRINCIPLE

This application is the National Stage of International Application PCT/FR96/02040, filed Dec. 23, 1996.

The present invention relates to novel forms of sustained-release (SR) microgranules containing Diltiazem as active principle.

Diltiazem is a calcium-antagonist benzothiazepine derivative which is useful for the treatment of arterial hypertension. It may be administered in various forms: tablets, injectable solutions or gelatin capsules containing sustained-release granules. The latter have the advantage of allowing the administration to be taken as a single dose required for daily treatment.

Various forms of Diltiazem SR microgranules have been described in the prior art, the most advantageous being that described in patent application EP-A-0,149,920, comprising a core combining Diltiazem with a water-soluble organic acid, in particular fumaric acid. The reason for this is that Diltiazem, or its pharmaceutically acceptable salts, are sparingly soluble at neutral or basic pH, and the presence of a water-soluble organic acid has proven to be particularly important, making it possible to create a buffered acidic microenvironment, promoting both the dilution and the absorption of the Diltiazem in areas of the digestive tract where the pH is too high. It has, nevertheless, been observed that for these SR forms, the solubilization and absorption of Diltiazem were dependent on the absorption of food, and are different when uptake of the microgranules is carried out on an empty stomach or during meals.

Organic-acid-free SR microgranules have been described in patent application EP-A-0,613,370. The core of the microgranules consists here of a neutral grain coated with a succession of layers of a water-soluble polymer, on the one hand, and of Diltiazem on the other hand.

For these various forms, the sustained release of the active principle is ensured by one or more layers coating the core of the microgranules, generally combining two types of film-forming polymer material, one being water-insoluble and the other water-soluble.

The present invention relates to a novel form of SR microgranules containing Diltiazem, or a pharmaceutically acceptable salt thereof, which is free of water-soluble organic acid, making it possible to obtain solubilization and absorption of the active principle which are at least equivalent to those obtained in the presence of an acid. In addition, the present invention relates to a simple novel form of SR microgranules containing Diltiazem, which is easy to prepare.

The microgranules according to the invention comprise a neutral granular support coated with an active layer comprising Diltiazem or a pharmaceutically acceptable salt thereof, a surfactant and a binder, and a layer which ensures sustained release of the active principle (referred to hereinbelow as the SR layer).

More particularly, the microgranules in accordance with the present invention may be of several categories.

The first category is represented by microgranules whose SR layer ensures slow sustained release of the active principle.

The second category is represented by microgranules whose SR layer ensures rapid sustained release of the active principle.

The difference between these two categories of monolayer microgranules lies essentially in the thickness of the coating agent contained in the SR layer. Indeed, the thicker this SR layer is, the slower will be the diffusion of the active principle.

The dissolution profile of each of these two types of microgranule is determined in vitro using water as dissolution medium, and gives the following specifications:

| Rapid microgranules: | | |
|---|---|---|
| Hours | Dissolution | Preferred Dissolution |
| 2 h | 0–45% | ≦30% |
| 6 h | ≧50% | ≧65% |

| Slow microgranules: | | |
|---|---|---|
| Hours | Dissolution | Preferred Dissolution |
| 12 h | 0–60% | ≦30% |
| 20 h | ≧50% | ≧45% |

| Mixture: | | |
|---|---|---|
| Hours | Dissolution | Preferred Dissolution |
| 1 h | ≦15% | ≦15% |
| 6 h | ≦55% | 25–55% |
| 10 h | 30–70% | 30–60% |
| 16 h | 30–85% | 55–85% |
| 22 h | — | ≧80% |

The present invention also relates to a third category of microgranules resulting from the coating of the SR layer which ensures slow sustained release of the active principle, that is to say of the SR layer of microgranules of the first category above, from another active layer comprising:
Diltiazem or a pharmaceutically acceptable salt thereof as active principle,
a surfactant, and
a binder,
itself coated with an external layer which ensures rapid sustained release of the active principle contained in this active layer.

In other words, these so-called "bilayer" microgranules consist, from the centre to the periphery, of a neutral granular support, of a first active layer, of an SR layer ensuring slow sustained release of the active principle contained in the first active layer, of a second active layer and of a SR layer ensuring rapid sustained release of the active principle contained in the second active layer.

It is understood that for the so-called "bilayer" microgranules, only the specifications described above and corresponding to the slow and mixed microgranules can be applied.

Advantageously, a so-called protective coating or intercalating layer is applied to the microgranule between the SR layer ensuring slow sustained release of the active principle and the second layer of active principle.

Indeed, it has been shown that during application of the second layer of Diltiazem, and/or during dissolution of the microgranules, interactions are established between the Diltiazem and the SR layer located between the two active layers, thereby leading to the modification of sustained release of the Diltiazem contained in the first active layer. This intercalating layer acts as it were as insulation between the two layers concerned, protecting them from each other. Another means of obtaining the same result would consist in using for the SR layer in question a coating agent which does not interact with the Diltiazem.

The neutral granular support consists of any pharmaceutically acceptable neutral granular support, with an average diameter of between 0.4 and 0.9 mm, preferably 0.4 and 0.6 mm. These are preferably grains consisting of sucrose and starch in a weight ratio in the region of 75/25, such as those described under the name "Sugar Spheres" (Handbook of Pharmaceutical Excipients, 2nd Ed., The Pharmaceutical Press, London, 1994).

The hydrochloride is preferably among the pharmaceutically acceptable salts of Diltiazem.

The surfactant may be an anionic, nonionic, cationic or amphoteric surfactant. It is preferably an anionic surfactant. Among the anionic surfactants are alkali metal ($C_{10}$–$C_{20}$) alkyl sulphates, preferably sodium lauryl sulphate, alkali metal ($C_{10}$–$C_{20}$)alkyl sulphonates or alkali metal ($C_{10}$–$C_{20}$) alkyl benzenesulphonates. The term alkali metal is preferably understood to refer to sodium or potassium.

The binder consists of any pharmaceutically acceptable binder which is useful for coating neutral granular supports, in particular pharmaceutically acceptable polymers such as the polyvinylpyrrolidones described under the name povidone (Handbook of Pharmaceutical Excipients, 2nd Ed., The Pharmaceutical Press, London, 1994), or hydroxypropyl methyl celluloses (HPMC), polyethylene glycols (PEG), etc.

The active layer comprising the Diltiazem may also comprise other common additives, such as a plasticizer.

In general, the active principle/neutral granular support weight ratio is in the region of 4/1. The term active principle is understood to refer to Diltiazem or the pharmaceutically acceptable salts thereof.

The active principle/surfactant weight ratio is advantageously between 99/1 and 95/5, preferably about 98/2.

The active principle/binder weight ratio is itself between 99/1 and 90/10, preferably in the region of 97/3.

The monolayer microgranules according to the invention preferably comprise the following components for the support and the active layer, the percentages being given on a weight basis for a total of 100:

| | |
|---|---|
| neutral granular support | 20–25% |
| active principle | 70–75% |
| surfactant | 0.5–5% |
| binder | 0.5–10% |
| plasticizer | 0–5%. |

The bilayer microgranules according to the invention preferably comprise the following components for the support and the active layers, the percentages being given on a weight basis for a total of 100:

| | |
|---|---|
| neutral granular support | 10–20% |
| active principle | 75–85% |
| surfactant | 0.5–5% |
| binder | 0.5–10% |
| plasticizer | 0.5–5%. |

Each SR layer consists of a coating agent which ensures the sustained release, optionally combined with one or more common additives, in particular a bioavailability adjuvant and/or a plasticizer and/or a lubricant.

The coating agent ensuring the sustained release is preferably a water-insoluble film-forming polymer, such as polymethacrylates (Handbook of Pharmaceutical Excipients, 2nd Ed., The Pharmaceutical Press, London 1994), in particular poly(ethyl acrylate, methyl methacrylate, trimethylammoniumethyl methacrylate chloride), which are marketed under the brand name Eudragit® RS.

The bioavailability adjuvant is preferably a fatty acid ester of polyoxyethylene, in particular those described under the name Polysorbate (Handbook of Pharmaceutical Excipients, 2nd Ed., The Pharmaceutical Press, London, 1994), in particular those marketed under the brand name Montanox®.

The lubricant consists of a pharmaceutically acceptable common lubricant used in the preparation of microgranules, in particular talc.

The plasticizer is a pharmaceutically acceptable common plasticizer used for the preparation of microgranules, in particular esters of citric, phthalic and sebacic acids, in particular aliphatic esters such as triethyl citrate, dibutyl sebacate or diethyl phthalate, and mixtures thereof.

Preferably, a phthalic acid ester is used for each active layer and a mixture of esters of citric and sebacic acids is used for each SR layer.

When it is present, the protective coating or intercalating layer consists of a methacrylic type polymer, a plasticizer, a lubricant and optionally a bioavailability adjuvant.

The monolayer microgranules according to the invention advantageously have the following final composition, the percentages being expressed on a weight basis for a total of 100%:

| | |
|---|---|
| neutral granular support | 10–20% |
| active layer: | |
| active principle | 45–65% |
| binder | 0.5–2% |
| surfactant | 0.5–1% |
| plasticizer | 0.5–1% |

| | |
|---|---|
| SR layer: | |
| coating agent | 10–30% |
| bioavailability adjuvant | 0.05–0.15% |
| plasticizer | 2–10% |
| lubricant | 2–10%. |

The bilayer microgranules according to the invention advantageously have the following final composition, the percentages being expressed on a dry weight basis for a total of 100%:

| | |
|---|---|
| neutral granular support | 10–20% |
| active layer: | |
| active principle | 45–60% |
| binder | 0.5–2% |
| surfactant | 0.5–1% |
| plasticizer | 0.5–1% |

| SR layer: | |
| --- | --- |
| coating agent | 10–30% |
| bioavailability adjuvant | 0.05–0.15% |
| plasticizer | 2–10% |
| lubricant | 2–10%. |

The active principle content of each active layer may be identical or different depending on the rate and the amount of active principle which it is desired to release over time. The necessary adaptations depending on the aim to be achieved are within the capability of any person skilled in the art.

The microgranules according to the invention are prepared according to the usual techniques for mounting the active principle onto the neutral granular support followed by coating with the SR layer, the operation being repeated for the bilayer microgranules.

The active principle is mounted by discontinuous spraying of an aqueous-alcoholic solution containing the binder, the surfactant and optionally the plasticizer, in alternance with sequences of dusting of the active principle and sequences of leaving to stand.

The Diltiazem microgranules thus obtained are then screened and dried.

Coating with each SR layer is then carried out by spraying an aqueous suspension containing the coating agent and the usual additives. The SR microgranules thus obtained are then screened and dried.

This operation of coating with each SR layer is repeated as many times as required to obtain the desired release kinetics.

Other characteristics of the microgranules according to the invention will become apparent on reading the examples which follow in which rotating turbomixers are preferably used, it also being possible to use any other coating machine, in particular one with a fluidized bed of the Glatt or Niro type, with the usual modifications known to those skilled in the art.

EXAMPLE 1

Figure 1:
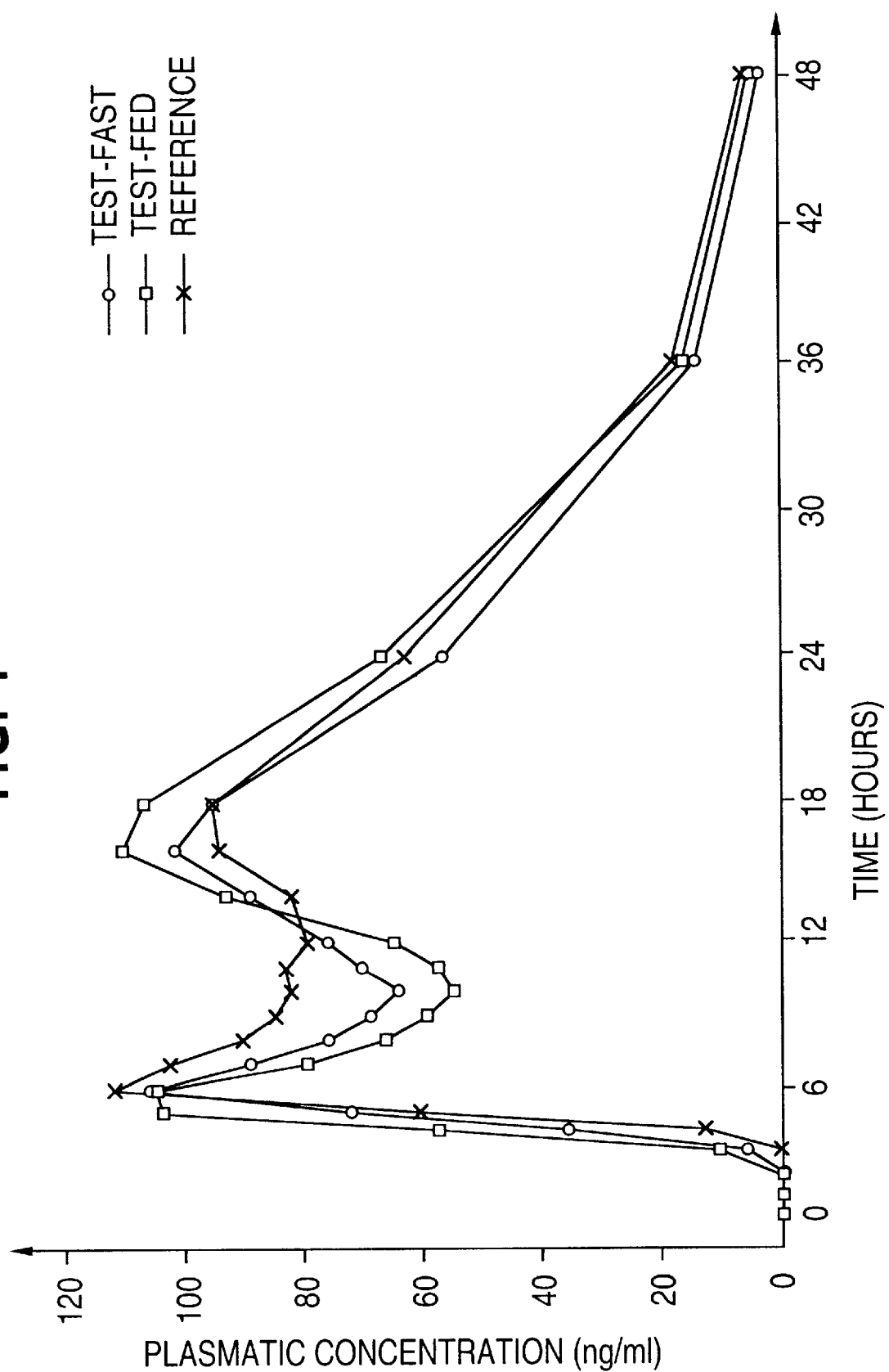
FIG. 1 shows a graphical comparison of diltiazem plasma concentrations for different administration regimens.

Preparation of Microgranules 1.1 Preparation of the Mounting Solution

The mounting excipients are weighed out in the following proportions:

| PVP K 17* (povidone) | 50% of the total DV |
| --- | --- |
| Sodium lauryl sulphate | 25% of the total DV |
| Diethyl phthalate | 25% of the total DV |
| Purified water | 50% of the total S |
| 95% ethyl alcohol | 50% of the total S |

*marketed by the company BASF

The 95% ethyl alcohol is poured into a first stainless steel mixer and the PVP K 17 is then introduced portionwise with stirring. Stirring is continued until the solution is homogeneous. An alcoholic 15% PVP K 17 solution is obtained.

The purified water is poured into a second stainless steel mixer and the sodium lauryl sulphate is then introduced portionwise with stirring. Stirring is continued until the solution is homogeneous. An aqueous 7.5% sodium lauryl sulphate solution is obtained.

The above two solutions are then mixed together and the diethyl phthalate is added with stirring.

1.2 Mounting of the Diltiazem

The support grains (sugar spheres) are placed in a rotating coating turbomixer. The active principle (hydrochloride) is mounted on the support grains by discontinuous spraying of the mounting suspension obtained above, in alternance with sequences of dusting of the active principle and sequences of leaving to stand. The dusting operation is repeated until the desired active principle content is obtained. The microgranules obtained are screened and are then dried.

Immediate-release microgranules of the following composition are obtained, the percentages being given on a weight basis:

| Diltiazem | 73.05% |
| --- | --- |
| support grains | 22.55% |
| PVP K 17 | 2.20% |
| sodium lauryl sulphate | 1.10% |
| diethyl phthalate | 1.10% | for a Diltiazem (hydrochloride) content of 735.75 mg/g of microgranules.

1.3 Preparation of the Coating Solution

The following coating excipients are weighed out in the proportions indicated:

| Eudragit RS 30 D* | DV* = 30.0% of the mass of Eudragit weighed out |
| --- | --- |
| Dibutyl sebacate | DV = 4.0% of the DV of Eudragit |
| Montanox 80 DF** | DV = 0.4% of the DV of Eudragit |
| Talc | DV = 20.0% of the DV of Eudragit |
| Triethyl citrate | DV = 16.0% of the DV of Eudragit |
| Purified water | S° = 50.0% of the mass of Eudragit weighed out |

*marketed by the company Rhöm Pharma
DV* = dry varnish or dry extract (which remains after evaporation of the solvents)
**distributed by the company Seppic
S° = solvent in which the excipients are dissolved or diluted.

The purified water is poured into a stainless steel beaker and the Montanox 80 DF, the triethyl citrate and then the dibutyl sebacate are introduced portionwise with stirring. Stirring is continued until the solution is homogeneous, and the talc is then introduced portionwise with stirring. Lastly, the Eudragit RS 30 D is added with stirring being continued until the suspension is homogeneous and then throughout the coating phase.

1.4 Coating of Microgranules

The microgranules obtained above are placed in a rotating coating turbomixer and they are then coated by continuous spraying of the solution obtained above. The mass of coated microgranules obtained is screened and they are then dried in a rotating turbomixer at room temperature, or by blowing with cold air if the room temperature is above 24° C.

This operational sequence is repeated as many times as required to obtain the desired kinetics.

Lastly, the SR microgranules obtained are lubricated by adding talc during the mixing phase.

EXAMPLE 2

By carrying out the process described in Example 1, varying the amount of Eudragit RS 30 D and of excipients, microgranules with the compositions described in Table I below are obtained.

TABLE I

| % | 1 | 2 | 3 | 4 | 5 | 6 | 7 | 8 | 9 |
|---|---|---|---|---|---|---|---|---|---|
| AP | 55.56 | 62.17 | 51.92 | 55.81 | 61.49 | 45.1 | 50.37 | 50.50 | 54.12 |
| N 30 | 17.08 | 19.19 | 16.03 | 17.23 | 18.98 | 13.92 | 15.55 | 15.59 | 16.71 |
| PVP | 1.86 | 1.87 | 1.56 | 1.98 | 1.85 | 1.36 | 1.52 | 1.52 | 1.63 |
| LAS | 0.93 | 0.94 | 0.78 | 0.84 | 0.93 | 0.68 | 0.76 | 0.76 | 0.81 |
| DP | 0.93 | 0.94 | 0.78 | 0.84 | 0.93 | 0.68 | 0.76 | 0.76 | 0.81 |
| E RS | 16.83 | 10.59 | 20.60 | 16.45 | 11.27 | 27.19 | 21.72 | 21.98 | 18.10 |
| D S | 2.73 | 0.42 | 0.83 | 0.66 | 0.44 | 1.12 | 0.88 | 0.88 | 0.72 |
| M 80 | 0.07 | 0.05 | 0.08 | 0.07 | 0.05 | 0.11 | 0.09 | 0.09 | 0.08 |
| Talc | 2.85 | 2.13 | 4.12 | 3.79 | 2.25 | 5.47 | 4.56 | 4.39 | 4.11 |
| TC | 1.15 | 1.71 | 3.31 | 2.64 | 1.81 | 4.37 | 3.49 | 3.53 | 2.91 |
| Total | | | | | 100% | | | | |
| mg/g | 555.63 | 599.55 | 504.51 | 516.05 | 602.03 | 452.62 | 497.29 | 482.36 | 536.31 |

The percentages are given on a dry microgranule weight basis, with the following abbreviations:
AP=active principle—Diltiazem hydrochloride;
N 30=neutral 30;
PVP=PVP K 17;
LAS=sodium lauryl sulphate;
DP=diethyl phthalate;
E RS=Eudragit RS 30 D;
DS=dibutyl sebacate;
M 80=Montanox 80 DF;
TC=triethyl citrate;
mg/g=Diltiazem content in mg per g of SR microgranules.

Microgranules 4 consist of a mixture of microgranules 2 and 3, lubricated with 0.5% talc (%=weight of talc/weight of microgranules to be lubricated).

Microgranules 5 are obtained by a second coating of 400 g of microgranules 2 with the suspension of Example 1.1.

Microgranules 6 are obtained by a second coating of 500 g of microgranules 2 with the suspension of Example 1.1.

Microgranules 7 consist of a mixture of microgranules 5 and 6, lubricated with 0.5% talc.

Microgranules 8 are obtained by a second coating of 400 g of microgranules 2 with the suspension of Example 1.1.

Microgranules 9 consist of a mixture of microgranules 5 and 8, lubricated with 0.5% talc.

EXAMPLE 3

Dissolution Kinetics

The above microgranules are subjected to a study of the kinetics of dissolution in water over 24 hours. The results obtained are summarized in Table II below, expressed as a percentage of active principle in solution relative to the total active principle.

TABLE II

| t(h) | 1 | 2 | 3 | 4 | 5 | 6 | 7 | 8 | 9 |
|---|---|---|---|---|---|---|---|---|---|
| 2 | 2.2 | 12.7 | 0.8 | 4.9 | 3.1 | 1.2 | 2.1 | 1.1 | 1.7 |
| 4 | 29.6 | 82.9 | 1.1 | 36.4 | 37.0 | 1.4 | 19.9 | 1.7 | 20.2 |
| 6 | — | 94.1 | 1.4 | 41.1 | 85.7 | 1.9 | 38.0 | 1.8 | 36.5 |
| 8 | — | 97.2 | 1.9 | 42.2 | 90.8 | 2.3 | 39.9 | 2.1 | 38.2 |
| 10 | — | 98.8 | 3.8 | 43.6 | 92.8 | 2.6 | 40.9 | 2.5 | 39.0 |
| 12 | 50.6 | 100 | 30.9 | 56.2 | 94.1 | 3.0 | 41.5 | 3.2 | 39.7 |
| 14 | 63.3 | — | 74.8 | 82.8 | 94.9 | 3.4 | 42.0 | 18.7 | 45.5 |
| 16 | — | — | 88.9 | 92.0 | 95.4 | 4.4 | 43.6 | 63.7 | 68.3 |
| 18 | 94.4 | — | 93.7 | 95.0 | 95.7 | 42.5 | 50.7 | 84.6 | 83.4 |
| 20 | — | — | 96.5 | 96.7 | 96.0 | 55.7 | 65.9 | 91.0 | 88.1 |
| 22 | — | — | — | 97.7 | 96.1 | 85.2 | 80.7 | 94.4 | 90.3 |
| 24 | 98.0 | — | — | 98.7 | — | — | 92.3 | — | 91.5 |

EXAMPLE 4

Bioequivalence with Cardizem® CD

The bioequivalence of gelatin capsules dosed with 300 mg of Diltiazem and containing the microgranules of composition 9 (Diltiazem CD) was compared in vivo with Cardizem® CD 300 mg marketed by the company Marion Merrell Dow Inc. in the United States.

The studies were carried out on three groups of 12 patients, by measuring the concentration of active principle in the plasma.

For the first group, the Cardizem® CD was administered on an empty stomach (reference).

For the second group, the Diltiazem CD was administered on an empty stomach ("test-fast").

For the third group, the Diltiazem CD was administered with simultaneous administration of a standardized meal, the American "breakfast" ("test-fed").

The average plasmatic concentration curves are reported in the appended FIG. 1.

This study unequivocally recognizes the bioequivalence of Diltiazem CD according to the invention with Cardizem® CD, independently of the simultaneous taking of food.

EXAMPLE 5

Preparation of Bilayer Microgranules 5.1—Bilayer Microgranules Free of Premounting Solution (Batch YED 006×1383.1)

A) Mounting of the First Layer of Diltiazem, Production of Batch YED 006.

a) Preparation of the Mounting Solution
Proportions of the excipients used:

| PVP K 17 | 50% of the total DV* |
|---|---|
| SODIUM LAURYL SULPHATE | 25% of the total DV |
| DIETHYL PHTHALATE | 25% of the total DV |
| PURIFIED WATER | 50% of the total S° |
| 95% ETHYL ALCOHOL | 50% of the total S |

DV* = dry varnish or dry extract (which remains after evaporation of the solvents).
S° = solvents in which the excipients are dissolved or diluted.

The solution is prepared in a stainless steel container,
The 95% ethyl alcohol and then the purified water are poured into the container and then stirred,
The PVP K 17 and then the lauryl sulphate are introduced successively and portionwise,
Stirring is continued until the PVP K 17 and the lauryl sulphate are completely dissolved,
The diethyl phthalate is then added and stirring is continued until the solution is homogeneous.

b) Mounting of the Diltiazem onto Neutral Support Grains

Neutral 30 support grains are placed in a rotating coating turbomixer,

The active principle is mounted on the Neutral 30 grains by discontinuous spraying of the suspension described above, in alternance with sequences of dusting of the Diltiazem and sequences of leaving to stand, The mass of microgranules obtained is screened through a grille with a mesh size ranging from 0.85 to 1.18 mm, The microgranules are then dried in the rotating turbomixer at room temperature and for 2 h 30 between two consecutive phases.

at 35° C. and for 4 to 6 h for the final mounting phase of each day. After drying, the turbomixer is left rotating for 4 h without any heat being applied.

The mass obtained is then lubricated with talc.

c) Formulation of the Microgranules after Mounting of the First Layer of Diltiazem

| Composition of the DV* | Amount in % |
| --- | --- |
| DILTIAZEM | 74.17 |
| NEUTRAL 30 | 21.26 |
| PVP K 17 | 2.16 |
| SODIUM LAURYL SULPHATE | 1.08 |
| DIETHYL PHTHALATE | 1.08 |
| TALC | 0.24 |
| Theoretical content | 741.7 mg/g |
| Content obtained | 735.9 mg/g |

DV* = dry varnish or dry extract (which remains after evaporation of the solvents).

B) Internal Coating of the Batch YED 006, Production of Batch YED 006×1383 a) Preparation of the Coating Suspension

Portions of the excipients used:

| AQUACOAT ECD 30 | DV* = 30.0% of the mass of Aquacoat weighed out |
| --- | --- |
| DIBUTYL SEBACATE | DV = 24.0% of the DV of Aquacoat |

DV* = dry varnish or dry extract (which remains after evaporation of the solvents).

The suspension is prepared in a stainless steel container into which the Aquacoat ECD 30 is introduced, The dibutyl sebacate is introduced portionwise into the stirred Aquacoat, Stirring is continued until the suspension is homogeneous (about 15 minutes).

b) Internal Coating of the Diltiazem Microgranules

The microgranules to be coated (obtained from batch YED 006) are placed in a coating turbomixer, The microgranules are coated by continuous spraying of the suspension described above, The mass of microgranules obtained is screened through a grille with a mesh size of 1.25 mm, The microgranules are then dried in a rotating turbomixer at a temperature of 40° C. for 2 h and then at room temperature for 7 h.

c) Formulation of Batch YED 006×1383 after Internal Coating

| Composition of the DV* | Amount in % |
| --- | --- |
| DILTIAZEM | 56.61% |
| NEUTRAL 30 | 16.22% |
| PVP K 17 | 1.65% |
| SODIUM LAURYL SULPHATE | 0.83% |
| DIETHYL PHTHALATE | 0.83% |
| AQUACOAT BCD 30 | 19.10% |
| DIBUTYL SEBACATE | 5.59% |
| TALC | 0.18% |
| Theoretical content | 566.1 mg/g |

DV* = dry varnish or dry extract (which remains after evaporation of the solvents).

C) Mounting of the Second Layer of Diltiazem on Batch YED 006×1383, Production of Batch YED 006×1383.1 a) Preparation of the Mounting Solution

Refer to paragraph A)a).

b) Mounting of the Diltiazem

The active principle is mounted on the microgranules obtained after coating of the batch YED 006×1383, by discontinuous spraying of the suspension described above, in alternance with sequences of dusting of the Diltiazem and sequences of leaving to stand, The mass of microgranules obtained screened through a grille with a mesh size of 1.50 mm, The microgranules are then dried in the rotating turbomixer at room temperature for 8 h.

c) Formulation of the Batch YED 006×1383.1 after Mounting of the Second Layer of Diltiazem

| Composition of the DV* | Amount in % |
| --- | --- |
| DILTIAZEM | 67.14% |
| NEUTRAL 30 | 11.54% |
| PVP 17 | 2.17% |
| SODIUM LAURYL SULPHATE | 1.09% |
| DIETHYL PHTHALATE | 1.09% |
| AQUACOAT ECD 30 | 13.59% |
| DIBUTYL SEBACATE | 3.26% |
| TALC | 0.13% |
| Theoretical content | 674.1 mg/g |

DV* = dry varnish or dry extract (which remains after evaporation of the solvents).

D) Outer Coating of the Batch YED 006×1383.1 a) Preparation of the Coating Suspension

Proportions of the excipients used:

| EUDRAGIT RS 30 D | DV* = 30.0% of the mass of Eudragit weighed out |
| --- | --- |
| DIBUTYL SEBACATE | DV = 4.0% of the DV of Eudragit |
| POLYSORBATE 80 | DV = 0.4% of the DV of Eudragit |
| TRIETHYL CITRATE | DV = 16.0% of the DV of Eudragit |
| TALC | DV = 10.0% of the DV of Eudragit |
| PURIFIED WATER | S° = 50.0% of the mass of Eudragit weighed out |

DV* = dry varnish or dry extract (which remains after evaporation of the solvents).
S° = solvent in which the excipients are dissolved or diluted.

The suspension is prepared in a stainless steel container into which the purified water is introduced, The Polysorbate 80, the triethyl citrate and the dibutyl sebacate (USP) are successively introdced portionwise into the stirred purified water, Stirring is continued until the solution is homogeneous (about 15 minutes),
The Eudragit RS 30 D is then added,
Stirring is continued until the mixture is homogeneous (about 15 minutes) and then throughout the coating.

b) Outer Coating of the Diltiazem Microgranules

The microgranules to be coated are placed in a coating turbomixer,
The microgranules are coated by continuous spraying of the suspension described above,
The mass of microgranules obtained is screened through a grille with a mesh size of 1.40 mm,
The microgranules are then dried in a rotating turbomixer at a temperature of 40° C. for 1 h and then at 30° C. for 8 h.

c) Formulation of Batch YED 006×1383.1 after External Coating

| Composition of the DV* | Amount in % |
|---|---|
| DILTIAZEM | 58.99% |
| NEUTRAL 30 | 10.14% |
| PVP K 17 | 1.91% |
| SODIUM LAURYL SULPHATE | 0.95% |
| DIETHYL PHTHALATE | 0.95% |
| EUDRAGIT RS 30 D | 8.62% |
| AQUACOAT ECD 30 | 11.94% |
| DIBUTYL SEBACATE | 3.22% |
| POLYSORBATE 80 | 0.04% |
| TALC | 1.84% |
| TRIETHYL CITRATE | 1.40% |
| Theoretical content | 589.9 mg/g |

DV* = dry varnish or dry extract (which remains after evaporation of the solvents).

E) Results of Dissolution after the Internal Coating, Mounting of the Second Layer of Diltiazem and the External Coating

| | YED 006 × 1381.1 | |
|---|---|---|
| YED 006 × 1383 Internal coating | Mounting of the second layer of Diltiazem | YED 006 × 1383.1 External coating |
| 1h | 1.38% | 38.87% | 0.68% |
| 2h | 9.45% | 42.38% | 1.82% |
| 3h | 20.33% | 51.98% | 8.49% |
| 4h | 28.82% | 58.82% | 28.41% |
| 5h | 34.99% | 63.15% | 37.67% |
| 6h | 39.84% | 66.26% | 41.68% |
| 7h | 43.92% | 68.66% | 45.31% |
| 8h | 47.37% | 70.64% | 48.64% |
| 9h | 50.58% | 72.23% | 51.51% |
| 10h | 53.27% | 73.75% | 54.00% |
| 11h | 55.77% | 74.92% | 56.12% |
| 12h | 57.96% | 76.21% | 58.23% |
| 13h | 59.96% | 77.27% | 59.89% |
| 14h | 61.94% | 78.18% | 61.63% |
| 15h | 63.62% | 78.97% | 63.14% |
| 16h | 65.30% | 79.80% | 64.56% |
| 17h | 66.62% | 80.56% | 66.06% |
| 18h | 68.25% | 81.32% | 67.42% |
| 19h | 69.52% | 82.15% | 68.78% |
| 20h | 70.79% | 82.88% | 70.21% |
| 21h | 71.95% | 83.36% | 71.57% |
| 22h | 73.12% | | 72.85% |
| 23h | 74.13% | | 74.02% |
| 24h | 75.10% | | 75.19% |

Percentages of Diltiazem dissolved at each hour of sampling

F) Formulations of Batch YED 006×1383.1
percentages given on a weight basis for a total of 100 (excluding coating):

| | YED 006 × 1383.1 |
|---|---|
| Mounting | |
| Active principle | 80.87% |
| Neutral support | 13.90% |
| Binder | 2.61% |
| Surfactant | 1.31% |
| Plasticizer | 1.31% | percentage on a dry weight basis for a total of 100% (final composition):

| | YED 006 × 1383.1 |
|---|---|
| Neutral support | 10.14% |
| Mounting | |
| Active principle | 58.99% |
| Binder | 1.91% |
| Surfactant | 0.95% |
| Plasticizer | 0.95% |
| Coating | |
| Coating agent | 20.56% |
| Bioavailability adjuvant | 0.04% |
| Plasticizer | 4.62% |
| Lubricant | 1.84% |

5.2—Bilayer Microgranules with Protective Coating Solution

I—Batch YED 005B×1350

A) Mounting of the First Layer of Diltiazem, Production of Batch YED 005 a) Preparation of the Mounting Solution

Refer to paragraph 5.1 A) a).

b) Mounting of Diltiazem on Neutral Support Grains

Refer to paragraph 5.1 A) b).

c) Formulation of Batch YED 005 after Mounting

| Composition of the DV* | Amount in % |
|---|---|
| DILTIAZEM | 74.65% |
| NEUTRAL 30 | 21.37% |
| PVP K 17 | 1.99% |
| SODIUM LAURYL SULPHATE | 1.00% |
| DIETHYL PHTHALATE | 1.00% |
| Theoretical content | 746.50 mg/g |
| Content obtained | 711.00 mg/g |

DV* = dry varnish or dry extract (which remains after evaporation of the solvents).

B) Internal Coating of Batch YED 005, Production of Batch YED 005 B a) Preparation of the Coating Suspension
Proportions of the excipients used:

| | |
|---|---|
| EUDRAGIT RS 30 D | DV* = 30.0% of the mass of Eudragit weighed out |
| DIBUTYL SEBACATE | DV = 4.0% of the DV of Eudragit |
| POLYSORBATE 80 | DV = 0.4% of the DV of Eudragit |
| TALC | DV = 10.0% of the DV of |

-continued

| | |
|---|---|
| TRIETHYL CITRATE | Eudragit<br>DV = 16.0% of the DV of Eudragit |
| PURIFIED WATER | S° = 50.0% of the mass of Eudragit weighed out |

DV* = dry varnish or dry extract (which remains after evaporation of the solvents).
S° = solvent in which the excipients are dissolved or diluted The suspension is prepared in a stainless steel container into which the purified water is introduced,
The Polysorbate 80, the triethyl citrate and the dibutyl sebacate (USP) are introduced successively and portionwise into the stirred purified water,
Stirring is continued until the solution is homogeneous (about 15 minutes),
The Eudragit RS 30 D is then added,
The talc is introduced portionwise into the suspension,
Stirring is continued until the mixture is homogeneous (about 15 minutes) and then throughout the coating,
An amount of talc equivalent to that placed in suspension will be prepared in order to be dusted onto the mass during the coating, b) Internal Coating of the Diltiazem Microgranules The microgranules to be coated (obtained from batch YED 005) are placed in a perforated turbomixer,
The microgranules are coated at a temperature of 30° C. by continuous spraying of the suspension described above, in alternance with sequences of dusting with talc (amount identical to that placed in suspension),
The mass of microgranules obtained is screened through a grille with a mesh size ranging from 1.18 to 1.25 mm,
The microgranules are then dried in a rotating turbomixer at a temperature of 30° C. for 1 h and then at 40° C. for 2 h,
The temperature is cooled to 30° C. before carrying out a second screening through a grille with a mesh size ranging from 1.18 to 1.25 mm,
The microgranules are then returned to the rotating turbomixer at a temperature of 30° C., throughout the period between the completed coating phase and the following one,
This operation sequence is repeated until the desired kinetics are obtained,
After the coating step, the microgranules are screened through a grille with a mesh size of 0.60 mm,
They are then lubricated with an amount of talc equivalent to 0.75% of the coated mass obtained.

c) Formulation of Batch YED 005 B after Internal Coating

| Composition of the DV* | Amount in % |
|---|---|
| DILTIAZEM | 53.20% |
| NEUTRAL 30 | 15.23% |
| PVP K 17 | 1.42% |
| SODIUM LAURYL SULPHATE | 0.71% |
| DIETHYL PHTHALATE | 0.71% |
| EUDRAGIT RS 30 D | 19.96% |
| DIBUTYL SEBACATE | 0.80% |
| POLYSORBATE 80 | 0.08% |
| TALC | 4.70% |
| TRIETHYL CITRATE | 3.19% |

-continued

| Composition of the DV* | Amount in % |
|---|---|
| Theoretical content | 532.0 mg/g |
| Content found | 537.3 mg/g |

DV* = dry varnish or dry extract (which remains after evaporation of the solvents).

C) Premounting of Batch YED 005 B, Production of Batch YED 005 B×1350 a) Preparation of the Premounting Suspension

Proportions of the excipients used:

| | |
|---|---|
| EUDRAGIT L 30 D | DV* = 30.0% of the mass of Eudragit weighed out |
| TALC | DV = 10.0% of the DV of Eudragit |
| TRIETHYL CITRATE | DV = 10.0% of the DV of Eudragit |
| PURIFIED WATER | S° = 50.0% of the mass of Eudragit weighed out |

DV* = dry varnish or dry extract (which remains after evaporation of the solvents).
S° = solvent in which the excipients are dissolved or diluted.

The suspension is prepared in a stainless steel container into which the purified water is introduced,
Triethyl citrate is introduced portionwise into the stirred purified water,
Stirring is continued until the solution is homogeneous (about 15 minutes),
The Eudragit L 30 D is then added,
The talc is introduced portionwise into the suspension,
Stirring is continued until the mixture is homogeneous (about 15 minutes) and then throughout the premounting.

b) Premounting of the Diltiazem Microgranules

The microgranules to be coated (obtained from batch YED 005 B) are placed in a coating turbomixer,
The microgranules are premounted by continuous spraying of the suspension described above,
The mass of microgranules obtained is screened through a grille with a mesh size of 1.50 mm,
The microgranules are then dried in a rotating turbomixer at a temperature of 40° C. for 1 h and then at room temperature for 7 h.

c) Formulation of Batch YED 005 B×1350 after Protective Coating

| Composition of the DV* | Amount in % |
|---|---|
| DILTIAZEM | 50.19% |
| NEUTRAL 30 | 14.36% |
| PVP K 17 | 1.34% |
| SODIUM LAURYL SULPHATE | 0.67% |
| DIETHYL PHTHALATE | 0.67% |
| EUDRAGIT RS 30 D | 18.83% |
| EUDRAGIT L 30 D | 4.72% |
| DIBUTYL SEBACATE | 0.75% |
| POLYSORBATE 80 | 0.08% |
| TALC | 4.91% |
| TRIETHYL CITRATE | 3.19% |
| Theoretical content | 501.9 mg/g |
| Content found | 521.0 mg/g |

DV* = dry varnish or dry extract (which remains after evaporation of the solvents).

D) Mounting of the Second Layer of Diltiazem on Batch YED 005 B×1350
a) Preparation of the Mounting Solution
   Refer to paragraph 5.1 A) a)
b) Mounting of the Diltiazem
   The active principle is mounted on microgranules obtained from the premounting, by discontinuous spraying of the suspension described above, in alternance with sequences of dusting of the Diltiazem and sequences of leaving to stand,
   The mass of microgranules obtained is screened through a grille with a mesh size of 1.50 mm,
   The microgranules are then dried in the rotating turbomixer at room temperature for 8 h.
c) Formulation of Batch YED 005×1350 after Mounting of the Second Layer of Diltiazem

| Composition of the DV* | Amount in % |
|---|---|
| DILTIAZEM | 61.40% |
| NEUTRAL 30 | 10.60% |
| PVP K 17 | 1.91% |
| SODIUM LAURYL SULPHATE | 0.95% |
| DIETHYL PHTHALATE | 0.95% |
| EUDRAGIT RS 30 D | 13.90% |
| EUDRAGIT L 30 D | 3.48% |
| DIBUTYL SEBACATE | 0.56% |
| POLYSORBATE 80 | 0.06% |
| TALC | 3.62% |
| TRIETHYL CITRATE | 2.57% |
| Theoretical content | 614.0 mg/g |

DV* = dry varnish or dry extract (which remains after evaporation of the solvents).

E) External Coating of Batch YED 005 B×1350
a) Preparation of the Coating Suspension
Proportions of the excipients used:

| EUDRAGIT RS 30 D | DV* = 30.0% of the mass of Eudragit weighed out |
| DIBUTYL SEBACATE | DV = 4.0% of the DV of Eudragit |
| POLYSORBATE 80 | DV = 0.4% of the DV of Eudragit |
| TRIETHYL CITRATE | DV = 16.0% of the DV of Eudragit |
| TALC | DV = 10.0% of the DV of Eudragit |
| PURIFIED WATER | S° = 50.0% of the mass of Eudragit weighed out |

DV* = dry varnish or dry extract (which remains after evaporation of the solvents).
S° = solvent in which the excipients are dissolved or diluted.

The suspension is prepared in a stainless steel container into which the purified water is introduced,
The Polysorbate 80, the triethyl citrate and the dibutyl sebacate (USP) are successively introduced portionwise into the stirred purified water,
Stirring is continued until the solution is homogeneous (about 15 minutes),
The Eudragit RS 30 D is then added,
Stirring is continued until the mixture is homogeneous (about 15 minutes) and then throughout the coating.
b) External Coating of the Diltiazem Microgranules
The microgranules to be coated are placed in a coating turbomixer,
The microgranules are coated by continuous spraying of the suspension described above,
The mass of microgranules obtained is screened through a grille with a mesh size of 1.50 mm,
The microgranules are then dried in a rotating turbomixer at a temperature of 40° C. for 1 h and then at room temperature for 7 h.
c) Formulation of Batch YED 005 B×1350 after External Coating

| Composition of the DV* | Amount in % |
|---|---|
| DILTIAZEM | 53.28% |
| NEUTRAL 30 | 9.20% |
| PVP K 17 | 1.65% |
| SODIUM LAURLYL SULPHATE | 0.83% |
| DIETHYL PHTHALATE | 0.83% |
| EUDRAGIT RS 30 D | 21.48% |
| EUDRAGIT L 30 D | 3.02% |
| DIBUTYL SEBACATE | 0.86% |
| POLYSORBATE 80 | 0.08% |
| TALC | 5.03% |
| TRIETHYL CITRATE | 3.74% |
| Theoretical content | 532.8 mg/g |

DV* = dry varnish or dry extract (which remains after evaporation of the solvents).

F) Results of Dissolution after the Internal Coating, Mounting of the Second Layer of Diltiazem and the External Coating

| | YED 005 B Internal coating | YED 005 B × 1350 Mounting of the second layer of Diltiazem | YED 005 B × 1350 External coating |
|---|---|---|---|
| 1h | 0.23% | 13.11% | 1.90% |
| 2h | 0.51% | 34.61% | 10.53% |
| 3h | 0.65% | 36.33% | 35.30% |
| 4h | 0.83% | 37.55% | 38.56% |
| 5h | 0.93% | 38.78% | 41.59% |
| 6h | 0.97% | 40.03% | 44.92% |
| 7h | 1.25% | 41.29% | 48.11% |
| 8h | 1.53% | 42.63% | 51.59% |
| 9h | 2.31% | 44.12% | 55.45% |
| 10h | 4.44% | 45.82% | 59.30% |
| 11h | 9.02% | 47.93% | 63.07% |
| 12h | 17.11% | 50.71% | 67.30% |
| 13h | 28.43% | 54.39% | 71.45% |
| 14h | 42.29% | 58.89% | 75.45% |
| 15h | 55.17% | 63.93% | 78.63% |
| 16h | 64.91% | 69.10% | 81.57% |
| 17h | 71.75% | 74.04% | 84.01% |
| 18h | 76.41% | 78.45% | 86.43% |
| 19h | 79.59% | 82.02% | |
| 20h | 81.65% | 84.85% | |
| 21h | 83.31% | 86.97% | |
| 22h | 84.69% | 88.66% | |
| 23h | 85.85% | 89.94% | |
| 24h | 86.81% | 90.98% | |

Percentages of Diltiazem dissolved at each hour of sampling

G) Formulations of Batch YED 005 B×1350
percentages given on a weight basis for a total of 100 (excluding coating):

| | YED 005 B × 1350 |
|---|---|
| Mounting | |
| Active principle | 80.99% |
| Neutral support | 13.98% |
| Binder | 2.52% |

-continued

| YED 005 B × 1350 | |
|---|---|
| Surfactant | 1.26% |
| Plasticizer | 1.26% | percentage on a dry weight basis for a total of 100% (final composition):

| | YED 005 B × 1350 |
|---|---|
| Neutral support | 9.20% |
| Mounting | |
| Active principle | 53.28% |
| Binder | 1.65% |
| Surfactant | 0.83% |
| Plasticizer | 0.83% |
| Coating | |
| Coating agent | 24.50% |
| Bioavailability adjuvant | 0.08% |
| Plasticizer | 4.60% |
| Lubricant | 5.03% |

II—Batch YED 006×1392.2
A) Mounting of the First Layer of Diltiazem, Production of Batch YED 006
a) Preparation of the Mounting Solution
   Refer to paragraph 5.1 A) a).
b) Mounting of the Diltiazem on Neutral Support Grains
Refer to paragraph 5.1 A) b),
The mass obtained is lubricated with talc.
c) Formulation of Batch YED 006 after Mounting of the First Layer of Diltiazem
   Refer to paragraph 5.1 B) a).
B) Internal Coating of Batch YED 006, Production of Batch YED 006 B
a) Preparation of the Coating Suspension
   Refer to paragraph 5.2 B) a).
b) Internal Coating of the Diltiazem Microgranules (First Step)
The microgranules to be coated (obtained from batch YED 006) are placed in a perforated turbomixer,
The microgranules are coated at a temperature of 30° C. by continuous spraying of the suspension described above, in alternance with sequences of dusting with talc (amount identical to that placed in suspension),
The mass of microgranules obtained is screened through a grille with a mesh size ranging from 1.18 to 1.25 mm,
The microgranules are then dried in a rotating turbomixer at a temperature of 30° C. for 1 h and then at 40° C. for 2 h,
The temperature is returned to 30° C. before carrying out a second screening through a grille with a mesh size ranging from 1.18 to 1.25 mm,
The microgranules are then returned to the rotating turbomixer at a temperature of 30° C., throughout the period between the completed coating phase and the following one,
This operational sequence is repeated until the desired kinetics are obtained,
After the coating step, the microgranules are screened through a grille with a mesh size of 0.60 mm,
They are then lubricated with an amount of talc equivalent to 0.75% of the coated mass obtained.

c) Formulation of Batch YED 006 B after Internal Coating

| Composition of the DV* | Amount in % |
|---|---|
| DILTIAZEM | 69.18% |
| NEUTRAL 30 | 19.83% |
| PVP K 17 | 2.02% |
| SODIUM LAURYL SULPHATE | 1.01% |
| DIETHYL PHTHALATE | 1.01% |
| EUDRAGIT RS 30 D | 4.66% |
| DIBUTYL SEBACATE | 0.19% |
| POLYSORBATE 80 | 0.02% |
| TALC | 1.35% |
| TRIETHYL CITRATE | 0.75% |
| Theoretical content | 691.8 mg/g |

DV* = dry varnish or dry extract (which remains after evaporation of the solvents).

C) Internal Coating of Batch YED 006 B, Production of Batch YED 006 B×1392
a) Preparation of the Coating Suspension
   Refer to paragraph 5.1 B) a).
b) Internal Coating of the Diltiazem Microgranules (Second Step)
The microgranules to be coated (obtained from batch YED 006 B) are placed in a perforated turbomixer,
The microgranules are coated by continuous spraying of the suspension described above,
The mass of microgranules obtained is screened through the grille with a mesh size ranging from 1.18 to 1.25 mm,
The microgranules are then dried in a rotating turbomixer at a temperature of 30° C. for 1 h and then at 40° C. for 2 h,
The temperature is returned to 30° C. before carrying out a second screening through a grille with a mesh size ranging from 1.18 to 1.25 mm,
The microgranules are then returned to the rotating turbomixer at a temperature of 30° C., throughout the period between the completed coating phase and the following one,
This operational sequence is repeated until the desired kinetics are obtained,
After the coating step, the microgranules are screened through a grille with a mesh size of 0.60 mm,
c) Formulation of Batch YED 006 B×1392 after Internal Coating

| Composition of the DV* | Amount in % |
|---|---|
| DILTIAZEM | 52.29% |
| NEUTRAL 30 | 14.99% |
| PVP K 17 | 1.53% |
| SODIUM LAURYL SULPHATE | 0.76% |
| DIETHYL PHTHALATE | 0.76% |
| EUDRAGIT RS 30 D | 20.91% |
| DIBUTYL SEBACATE | 0.84% |
| POLYSORBATE 80 | 0.08% |
| TALC | 4.49% |
| TRIETHYL CITRATE | 3.35% |
| Theoretical content | 522.9 mg/g |

DV* = dry varnish or dry extract (which remains after evaporation of the solvents).

D) Premounting of Batch YED 006 B×1392, Production of Batch YED 006 B×1392.2
a) Preparation of the Premounting Suspension Proportions of the excipients used:

| | |
|---|---|
| EUDRAGIT L 30 D | DV* = 30.0% of the mass of Eudragit weighed out |
| TRIETHYL CITRATE | DV = 10.0% of the DV of Eudragit |
| PURIFIED WATER | S° = 20.0% of the inass of Eudragit weighed out |

DV* = dry varnish or dry extract (which reznains after evaporation of the solvents).
S° = solvent in which the excipients are dissolved or diluted.

The suspension is prepared in a stainless steel container into which the purified water is introduced,
The triethyl citrate is introduced portionwise into the stirred purified water,
Stirring is continued until the solution is homogeneous (about 15 minutes),
The Eudragit L 30 D is then added,
Stirring is continued until the mixture is homogeneous (about 15 minutes) and then throughout the premounting.

b) Premounting of the Diltiazem Microgranules

The microgranules to be coated are placed in a perforated turbomixer,
The microgranules are premounted at a tempertare of 30° C. by continuous spraying of the suspension described above,
The mass of microgranules obtained is screened through a grille with a mesh size of 1.40 mm,
The microgranules are then dried in a rotating turbomixer at a temperature of 35° C. for 10 h.

c) Formulation of Batch YED 006 Bx1392.2 after Premounting

| Composition of the DV* | Amount in % |
|---|---|
| DILTIAZEM | 50.19% |
| NEUTRAL 30 | 14.36% |
| PVP K 17 | 1.34% |
| SODIUM LAURYL SULPHATE | 0.67% |
| DIETHYL PHTHALATE | 0.67% |
| EUDRAGIT RS 30 D | 18.83% |
| EUDRAGIT L 30 D | 4.72% |
| DIBUTYL SEBACATE | 0.75% |
| POLYSORBATE 80 | 0.08% |
| TALC | 4.91% |
| TRIETHYL CITRATE | 3.19% |
| Theoretical content | 501.9 mg/g |

DV* = dry varnish or dry extract (which remains after evaporation of the solvents).

E) Mounting of the Second Layer of Diltiazem on Batch YED 006 Bx1392.2 a) Preparation of the Mounting Solution

Refer to paragraph 5.2 A) a).

b) Mounting of the Diltiazem

The active principle is mounted on the microgranules obtained from the protective coating of batch YED 006 Bx1392.2, by discontinuous spraying of the suspension described above, in alternance with sequences of dusting of the Diltiazem and sequences of leaving to stand,
The mass of microgranules obtained is screened through a grille with a mesh size of 1.50 mm,
The microgranules are then dried in the rotating turbomixer at room temperature for 8 h.

c) Formulation of Batch YED 006 Bx1392.2 after Mounting of the Second Layer of Diltiazem

| Composition of the DV* | Amount in % |
|---|---|
| DILTIAZEM | 58.75% |
| NEUTRAL 30 | 10.11% |
| PVP K 17 | 1.85% |
| SODIUM LAURYL SULPHATE | 0.93% |
| DIETHYL PHTHALATE | 0.92% |
| EUDRAGIT RS 30 D | 14.11% |
| EUDRAGIT L 30 D | 6.75% |
| DIBUTYL SEBACATE | 0.56% |
| POLYSORBATE 80 | 0.06% |
| TALC | 3.03% |
| TRIETHYL CITRATE | 2.93% |
| Theoretical content | 587.5 mg/g |

DV* = dry varnish or dry extract (which remains after evaporation of the solvents).

F) External Coating of Batch YED 006 Bx1392.2 a) Preparation of the Coating Suspension

Refer to paragraph 5.2 B) a).

b) External Coating of the Diltiazem Microgranules

The microgranules to be coated are placed in a perforated turbomixer,
The microgranules are coated by continuous spraying of the suspension described above,
The mass of microgranules obtained is screened through a grille with a mesh size ranging from 1.18 to 1.25 mm,
The microgranules are then dried in a rotating turbomixer at a temperature of 30° C. for 1 h and then 40° C. for 2 h,
The temperature is returned to 30° C. before carrying out a second screening through a grille with a mesh size ranging from 1.18 to 1.25 mm,
The microgranules are then returned to the rotating turbomixer at a temperature of 30° C., throughout the period between the completed coating phase and the following one,
This operational sequence is repeated until the desired kinetics are obtained,
After the coating step, the microgranules are screened through a grille with a mesh size of 0.60 mm,
They are then lubricated with an amount of talc equivalent to 1.5% of the coated mass obtained.

c) Formulation of Batch YED 006 Bx1392.2 after External Coating

| Composition of the DV* | Amount in % |
|---|---|
| DILTIAZEM | 49.71% |
| NEUTRAL 30 | 8.56% |
| PVP K 17 | 1.57% |
| SODIUM LAURYL SULPHATE | 0.78% |
| DIETHYL PHTHALATE | 0.78% |
| EUDRAGIT RS 30 D | 21.89% |
| EUDRAGIT L 30 D | 5.71% |
| DIBUTYL SEBACATE | 0.88% |
| POLYSORBATE 80 | 0.09% |
| TALC | 5.97% |
| TRIETHYL CITRATE | 4.08% |
| Theoretical content | 497.1 mg/g |

DV* = dry varnish or dry extract (which remains after evaporation of the solvents).

G) Results of Dissolution after Internal Coating and External Coating (in Two Media)

|  | H₂O medium<br>YED 006 B × 1392<br>Internal coating | H₂O media pH 7<br>YED 006 B × 1392.2<br>External coating | |
|---|---|---|---|
| 1 h | 0.61% | 1.08% | 1.46% |
| 2 h | 0.84% | 3.37% | 5.60% |
| 3 h | 0.99% | 12.73% | 16.72% |
| 4 h | 1.14% | 25.42% | 21.59% |
| 5 h | 1.29% | 31.93% | 22.82% |
| 6 h | 1.44% | 34.07% | 23.43% |
| 7 h | 1.67% | 35.09% | 23.85% |
| 8 h | 1.90% | 35.78% | 24.31% |
| 9 h | 2.66% | 36.47% | 24.62% |
| 10 h | 4.63% | 37.02% | 25.04% |
| 11 h | 10.38% | 37.42% | 25.53% |
| 12 h | 22.73% | 37.96% | 26.07% |
| 13 h | 40.08% | 38.41% | 26.83% |
| 14 h | 57.50% | 38.93% | 27.71% |
| 15 h | 71.26% | 39.39% | 28.93% |
| 16 h | 80.11% | 39.79% | 30.34% |
| 17 h | 85.78% | 40.17% | 32.39% |
| 18 h | 89.03% | 40.62% | 35.14% |
| 19 h | 91.07% | 41.22% | 38.47% |
| 20 h | 92.65% | 41.77% | 42.07% |
| 21 h | 93.65% | 42.38% | 45.81% |
| 22 h |  | 43.22% | 49.47% |
| 23 h |  | 43.84% | 52.74% |
| 24 h |  | 44.74% | 55.79% |

Percentages of Diltiazem dissolved at each hour of sampling

H) Formulations of Batch YED 006×1392.2 percentages given on a weight basis for a total of 100 (excluding coating):

|  | YED 006 × 1392.2 |
|---|---|
| Mounting | |
| Active principle | 80.96% |
| Neutral support | 13.93% |
| Binder | 2.55% |
| Surfactant | 1.28% |
| Plasticizer | 1.27% | percentage on a dry weight basis for a total of 100% (final composition):

|  | YED 006 × 1392.2 |
|---|---|
| Neutral support | 8.56% |
| Mounting | |
| Active principle | 49.71% |
| Binder | 1.57% |
| Surfactant | 0.78% |
| Plasticizer | 0.78% |
| Coating | |
| Coating agent | 27.59% |
| Bioavailability adjuvant | 0.09% |
| Plasticizer | 4.96% |
| Lubricant | 5.97% |

EXAMPLE 6
Preparation of Monolayer Microgranules

A) Mounting of the Diltiazem, Production of Batch YED 001 a) Preparation of the Mounting Solution

Proportions of the excipients used:

| PVP K 17 | 50% of the total DV* | DV = 15% of the weight of the solution |
| SODIUM LAURYL SULPHATE | 25% of the total DV | |
| DIETHYL PHTHALATE | 25% of the total DV | S = 85% of the weight of the solution |
| PURIFIED WATER | 50% of the total S° | |
| 95% ETHYL ALCOHOL | 50% of the total S | |

DV* = dry varnish or dry extract (which remains after evaporation of the solvents).
°S = solvents in which the excipients are dissolved or diluted.

The solution is prepared in a stainless steel container,

The 95% ethyl alcohol and then the purified water are poured into the container and then stirred, The PVP K 17 and then the lauryl sulphate are successively introduced portionwise, Stirring is continued until the PVP K 17 and the lauryl sulphate have completely dissolved, The diethyl phthalate is then added and stirring is continued until the solution is homogeneous.

b) Mounting of the Diltiazem on the Neutral Support Grains

Neutral 30 support grains are placed in a rotating coating turbomixer,

The active principle is mounted on the Neutral 30 grains by discontinuous spraying of the solution described above, in alternance with sequences of dusting of the Diltiazem and sequences of leaving to stand, The mass of microgranules obtained is screened through a grille with a mesh size ranging from 0.71 to 1.00 mm, The microgranules are then dried in the rotating turbomixer at room temperature for 3 to 8 h.

c) Formulation of Batch YED 001 after Mounting

| Composition of the DV* | Amount in % |
|---|---|
| DILTIAZEM | 73.05% |
| NEUTRAL 30 | 22.55% |
| PVP K 17 | 2.20% |
| SODIUM LAURYL SULPHATE | 1.10% |
| DIETHYL PHTHALATE | 1.10% |
| Theoretical content | 730.50 mg/g |
| Content obtained | 735.75 mg/g |

DV* = dry varnish or dry extract (which remains after evaporation of the solvents).

B) Coating of Batch YED 001, Production of Batches YED 001 A1 and YED 001 B1

After separation of the mass of microgranules obtained on mounting (proportions: 45%/55% w/w), the two masses are coated separately with different amounts of excipients.

a) Preparation of the Coating Suspension

Proportions of the excipients used:

| EUDRAGIT RS 30 D | DV* = 30.0% of the mass of Eudragit weighed out |
| DIBUTYL SEBACATE | DV = 4.0% of the DV of Eudragit |
| Polysorbate 80 | DV = 0.4% of the DV of Eudragit |
| TRIETHYL CITRATE | DV = 16.0% of the DV of Eudragit |
| TALC | DV* = 10.0% of the DV of Eudragit |
| PURIFIED WATER | S° = 50.0% of the mass of Eudragit weighed out |

DV* = dry varnish or dry extract (which remains after evaporation of the solvents).
°S = solvent in which the excipients are dissolved or diluted.

The suspension is prepared in a stainless steel container into which the purified water is introduced, The Polysorbate 80, the triethyl citrate and the dibutyl sebacate (USP) are successively introduced portionwise into the stirred purified water,
Stirring is continued until the suspension is homogeneous (about 15 minutes),
The Eudragit RS 30 D and the talc are then added,
Stirring is continued until the mixture is homogeneous (about 15 minutes) and then throughout the coating.

b) Coating of the Diltiazem Microgranules

The microgranules to be coated (obtained from batch YED 001) are placed in a coating turbomixer,
The microgranules are coated at a temperature of 30° C. by continuous spraying of the suspension described above, in alternance with sequences of dusting with talc (DV=20% of the DV of Eudragit),
The mass of microgranules obtained is screened through a grille with a mesh size ranging from 1.00 to 1.12 mm,
The microgranules are then dried in a rotating turbomixer at room temperature, throughout the period between the completed coating phase and the following one,
This operational sequence is repeated until the desired kinetics for batches A1 and B1 are obtained.

c) Formulation of Batches YED 001 A1 and YED 001 B1 after Coating, YED 001 M3 Mixture After the coating steps, a fraction of the granules obtained from batch YED 001 A1 and a fraction of the granules obtained from batch YED 001 B1 are mixed together and lubricated with talc (DV of talc=0.50% of the total mass mixed),
The mixture is made such that the amount of active principle provided by batch YED 001 A1 is equal to 40% of the total amount of active principle in the mixture. The remaining 60% are provided by batch YED 001 B1.

| Composition of the DV* | Batch | | |
|---|---|---|---|
| | YET 001A1 | YED 001B1 | YED 001M3 |
| | Amount in % | | |
| DILTIAZEM | 61.5% | 45.1% | 50.4% |
| NEUTRAL 30 | 19.0% | 13.9% | 15.5% |
| PVP K 17 | 1.9% | 1.4% | 1.5% |
| SODIUM LAURYL SULPHATE | 0.9% | 0.7% | 0.8% |
| DIETHYL PHTHALATE | 0.9% | 0.7% | 0.8% |
| EUDRAGIT RS 30 D | 11.3% | 27.2% | 21.7% |
| DI.BUTYL SEBACATE | 0.4% | 1.1% | 0.9% |
| POLYSORBATE 80 | 0.1% | 0.1% | 0.1% |
| TALC | 2.3% | 5.5% | 4.9% |
| TRIETHYL CITRATE | 1.8% | 4.4% | 3.5% |
| Theoretical content | 615 mg/g | 451 mg/g | 504 mg/g |
| Content found | 602 mg/g | 453 mg/g | 497 mg/g |

DV* = dry varnish or dry extract (which remains after evaporation of the solvents).

C) Results of Dissolution of Batches YED 001A1, YED 001B1, YED 001M3, 8175 (Gelatin Capsules of Batch YED 001M3 Containing a 300 mg Dose)

| | YED 001 A1 | YED 001B1 | YED 001M3 | 8175 (YED 001M3) |
|---|---|---|---|---|
| 1 h | 0.60% | 0.75% | 0.50% | 1.01% |
| 2 h | 3.06% | 1.20% | 2.10% | 3.36% |
| 3 h | 10.69% | 1.27% | 6.70% | 12.37% |
| 4 h | 37.01% | 1.42% | 19.90% | 26.77% |
| 5 h | 72.92% | 1.71% | 33.80% | 37.05% |
| 6 h | 85.68% | 1.93% | 38.00% | 40.37% |
| 7 h | 89.04% | 2.15% | 39.20% | 41.49% |
| 8 h | 90.77% | 2.29% | 39.90% | 42.19% |
| 9 h | 91.97% | 2.43% | 40.50% | 42.69% |
| 10 h | 92.79% | 2.57% | 40.90% | 43.10% |
| 11 h | 93.61% | 2.72% | 41.20% | 43.62% |
| 12 h | 49.14% | 3.00% | 41.50% | 44.18% |
| 13 h | 94.53% | 3.21% | 41.70% | 44.72% |
| 14 h | 94.90% | 3.43% | 42.00% | 45.30% |
| 15 h | 95.12% | 3.78% | 42.50% | 46.06% |
| 16 h | 95.35% | 4.43% | 43.60% | 46.81% |
| 17 h | 95.50% | 6.24% | 45.60% | 47.91% |
| 18 h | 95.65% | 12.46% | 50.70% | 50.80% |
| 19 h | 95.73% | 31.04% | 58.00% | 57.72% |
| 20 h | 95.95% | 55.72% | 65.90% | 69.03% |
| 21 h | 96.03% | 75.14% | 73.20% | 81.44% |
| 22 h | 96.10% | 85.19% | 80.70% | 90.49% |
| 23 h | | | 87.50% | 95.46% |
| 24 h | | | 92.30% | 98.12% |

Percentages of Diltiazem dissolved at each hour of sampling

D) Formulations of Batch YED 001 M3 percentages given on a weight basis for a total of 100 (excluding coating):

| Mounting | YED 001 M3 |
|---|---|
| Active principle | 73.05% |
| Neutral support | 22.55% |
| Binder | 2.20% |
| Surfactant | 1.10% |
| Plasticizer | 1.10% | percentage on a dry weight basis for a total of 100% (final composition):

| | YED 001 M3 |
|---|---|
| Neutral support | 15.55 |
| Mounting | |
| Active principle | 50.37% |
| Binder | 1.52% |
| Surfactant | 0.76% |
| Plasticizer | 0.76% |
| Coating | |
| Coating agent | 21.72% |
| Bioavailability adjuvant | 0.09% |
| Plasticizer | 4.37% |
| Lubricant | 4.86% |

EXAMPLE 7

Preparation of Monolayer Microgranules

A) Mounting of Diltiazem, Production of Batches YED 004 and YED 005 a) Preparation of the Mounting Soultion
Proportions of the excipients used:

| PVP K 17 | 50% of the total DV* | |
| SODIUM LAURYL SULPHATE | 25% of the total DV | DV = 20% of the weight of the solution |
| DIETHYL PHTHALATE | 25% of the total DV | |

-continued

| | | |
|---|---|---|
| PURIFIED WATER | 50% of the total S° | S = 20% of the weight of the solution |
| 95% ETHYL ALCOHOL | 50% of the total S | |

DV* = dry varnish or dry extract (which remains after evaporation of the solvents).
°S = solvent in which the excipients are dissolved or diluted.

The solution is prepared in a stainless steel container,
The 95% ethyl alcohol and then the purified water are poured into the container and then stirred,
The PVP K 17 and then the lauryl sulphate are successively introduced portionwise,
Stirring is continued until the PVP K 17 and the lauryl sulphate have completely dissolved,
The diethyl phthalate is then added and stirring is continued until the solution is homogeneous.

b) Mounting of the Diltiazem on the Neutral Support Grains

Neutral 30 support grains are placed in a rotating coating turbomixer,
The active principle is mounted on the Neutral 30 grains by discontinuous spraying of the suspension described above, in alternance with sequences of dusting of the Diltiazem and sequences of leaving to stand,
The mass of microgranules obtained is screened through a grille with a mesh size ranging from 0.85 to 1.18 mm,
The microgranules are then dried in the rotating turbomixer.
  YED 004: at 35° C. for 12 to 14 h,
  YED 005:
    At room temperature for 2 h 30 between two consecutive phases.
    At 35° C. for 4 to 6 h for the final mounting phase of each day.
    After drying, the turbomixer is left rotating for 4 h without any heat being supplied.

c) Formulation of Batches YED 004 and YED 005 after Mounting

| | BATCH | |
|---|---|---|
| Composition of the DV* | YED 004 Amount in % | YED 005 Amount in % |
| DILTIAZEM | 73.94 | 74.65 |
| NEUTRAL 30 | 21.20 | 21.37 |
| PVP K 17 | 2.43 | 1.99 |
| SODIUM LAURYL SULPHATE | 1.21 | 1.00 |
| DIETHYL PHTHALATE | 1.21 | 1.00 |
| THEORETICAL CONTENT | 739.4 mg/g | 746.5 mg/g |
| CONTENT OBTAINED | 727.8 mg/g | 711.0 mg/g |

DV* = dry varnish or dry extract (which remains after evaporation of the solvents).

B) Coating of Batches YED 004 and YED 005, Production of Batches YED 004A and YED 005B After separation of the masses of microgranules obtained on mounting (proportions: 40%/60% w/w), two of the masses YED 004A (40% of YED 004) and YED 005B (60% of YED 005) are coated separately with different amounts of excipients.

a) Preparation of the Coating Suspension

Proportions of the excipients used:

| | |
|---|---|
| EUDRAGIT RS 30 D | DV* = 30.0% of the mass of Eudragit weighed out |
| DIBUTYL SEBACATE | DV = 4.0% of the DV of Eudragit |
| Polysorbate 80 | DV = 0.4% of the DV of Eudragit |
| TALC | DV = 10.0% of the DV of Eudragit |
| TRIETHYL CITRATE | DV = 16.0% of the DV of Eudragit |
| PURIFIED WATER | S° = 50.0% of the mass of Eudragit weighed out |

DV* = dry varnish or dry extract (which remains after evaporation of the solvents).
°S = solvent in which the excipients are dissolved or diluted.

The suspension is prepared in a stainless steel container into which the purified water is introduced,
The Polysorbate 80, the triethyl citrate and the dibutyl sebacate (USP) are successively introduced portionwise into the stirred purified water,
Stirring is continued until the suspension is homogeneous (about 15 minutes),
The Eudragit RS 30 D is then added,
The talc is introduced portionwise into the suspension,
Stirring is continued until the mixture is homogeneous (about 15-minutes) and then throughout the coating, b) Coating of the Diltiazem Microgranules The microgranules to be coated (obtained from batches YED 004 and YED 005) are placed in a perforated turbomixer,
The microgranules are coated at a temperature of 30° C. by continuous spraying of the suspension described above,
The mass of microgranules obtained is screened through a grille with a mesh size ranging from 1.18 to 1.25 mm,
The microgranules are then dried in a rotating turbomixer at a temperature of 30° C. for 1 h and then at 40° C. for 2 h,
The temperature is returned to 30° C. before carrying out a second screening through a grille with a mesh size ranging from 1.18 to 1.25 mm,
The microgranules are then returned to the rotating turbomixer at a temperature of 30° C., throughout the period between the completed coating phase and the following one,
This operational sequence is repeated until the desired kinetics are obtained,
After the coating step, the microgranules are screened through a grille with a mesh size of 0.60 mm,
They are then lubricated with an amount of talc equivalent to 0.75% of the coated mass obtained.

c) Formulation of Batches YED 004A and YED 005B after Coating, YED 005M Mixture

A fraction of the granules obtained from batch YED 004A and a fraction of the granules obtained from batch YED 005B are mixed together,
The mixture is made such that the amount of active principle provided by batch YED 004A is equal to 40% of the total amount of active principle in the mixture. The remaining 60% are provided by batch YED 005B.

| | BATCH | | |
|---|---|---|---|
| Composition of the DV* | YED 004A Amount in % | YED 005B Amount in % | YED 005M Amount in % |
| DILTIAZEM | 65.37 | 53.20 | 57.43 |
| NEUTRAL 30 | 18.75 | 15.23 | 16.45 |

-continued

| Composition of the DV* | BATCH | | |
|---|---|---|---|
| | YED 004A Amount in % | YED 005B Amount in % | YED 005M Amount in % |
| PVP K 17 | 2.15 | 1.42 | 1.68 |
| SODIUM LAURYL SULPHATE | 1.07 | 0.71 | 0.84 |
| DIETHYL PHTHALATE | 1.07 | 0.71 | 0.84 |
| EUDRAGIT RS 30 D | 7.74 | 19.96 | 15.67 |
| DIBUTYL SEBACATE | 0.31 | 0.80 | 0.63 |
| POLYSORBATE 80 | 0.04 | 0.08 | 0.07 |
| TALC | 2.27 | 4.70 | 3.91 |
| TRIETHYL CITRATE | 1.24 | 3.19 | 2.51 |
| THEORETICAL CONTENT | 654 mg/g | 532 mg/g | 574 mg/g |
| CONTENT FOUND | 656 mg/g | 537 mg/g | 540 mg/g |

DV* = dry varnish or dry extract (which remains after evaporation of the solvents).

C) Results of Dissolution of Batches YED 004A, YED 005B, YED 005M, 8394 (Gelatin Capsules of Batch YED 005M Containing a 300 mg Dose)

| | YED 004A | YED 005B | YED 005M | 8394 |
|---|---|---|---|---|
| 1 h | 3.99 | 0.26 | 2.15 | 2.31 |
| 2 h | 11.32 | 0.56 | 6.25 | 6.85 |
| 3 h | 32.46 | 0.72 | 16.70 | 19.15 |
| 4 h | 65.74 | 0.92 | 30.03 | 33.44 |
| 5 h | 85.57 | 1.02 | 35.81 | 39.44 |
| 6 h | 92.79 | 1.07 | 37.60 | 41.49 |
| 7 h | 95.83 | 1.38 | 38.52 | 42.54 |
| 8 h | 97.58 | 1.69 | 39.18 | 43.24 |
| 9 h | 99.07 | 2.55 | 39.84 | 43.98 |
| 10 h | 100.21 | 4.90 | 40.61 | 44.83 |
| 11 h | 100.98 | 9.96 | 42.40 | 46.23 |
| 12 h | 101.80 | 18.90 | 45.62 | 48.74 |
| 13 h | 102.26 | 31.41 | 51.18 | 52.71 |
| 14 h | 102.77 | 46.73 | 58.46 | 58.53 |
| 15 h | 103.08 | 60.96 | 67.33 | 65.63 |
| 16 h | 103.23 | 71.72 | 75.60 | 73.50 |
| 17 h | 103.70 | 79.27 | 82.28 | 80.27 |
| 18 h | 103.69 | 84.42 | 87.18 | 85.46 |
| 19 h | 103.90 | 87.94 | 90.44 | 89.21 |
| 20 h | 103.90 | 90.21 | 92.66 | 97.88 |
| 21 h | 103.90 | 92.05 | 94.39 | 93.75 |
| 22 h | 103.95 | 93.58 | 95.67 | 95.15 |
| 23 h | 103.89 | 94.85 | 96.73 | 96.30 |
| 24 h | 103.94 | 95.92 | 97.70 | 97.29 |

Percentages of Diltiazem dissolved at each hour of sampling

D) Formulations of Batch YED 005 M percentages given on a weight basis for a total of 100 (excluding coating):

| | YED 005 M |
|---|---|
| Mounting | |
| Active principle | 74.37% |
| Neutral support | 21.30% |
| Binder | 2.17% |
| Surfactant | 1.08% |
| Plasticizer | 1.08% | percentage on a dry weight basis for a total of 100% (final composition):

| | YED 005 M |
|---|---|
| Neutral support | 16.45% |
| Mounting | |
| Active principle | 57.43% |
| Binder | 1.68% |
| Surfactant | 0.84% |
| Plasticizer | 0.84% |
| Coating | |
| Coating agent | 15.67% |
| Bioavailability adjuvant | 0.07% |
| Plasticizer | 3.13% |
| Lubricant | 3.91% |

EXAMPLE 8

Preparation of Bilayer Microgranules

A) Mounting of the First Layer of Diltiazem, Production of Batch YED 005

Refer to paragraph A) of Example 5.1.

B) Internal Coating of Batch YED 005, Production of Batch YED 005×1406 a) Preparation of the Coating Suspension

Refer to paragraph I B)a) of Example 5.2.

b) Internal Coating of the Diltiazem Microgranules

The microgranules to be coated are placed in a coating turbomixer,

The microgranules are coated by continuous spraying of the suspension described above, The mass of microgranules obtained is screened through a grille with a mesh size of 1.50 mm, The microgranules are then dried in a rotating turbomixer at a temperature of 40° C. for 2 h.

c) Formulation of Batch YED 005×1406 after Internal Coating

| Composition of the DV* | Amount in % |
|---|---|
| DILTIAZEM | 58.12 |
| NEUTRAL 30 | 16.63 |
| PVP K 17 | 1.55 |
| SODIUM LAURYL SULPHATE | 0.78 |
| DIETHYL PHTHALATE | 0.78 |
| EUDRAGIT RS 30 D | 15.61 |
| DIBUTYL SEBACATE | 0.62 |
| POLYSORBATE 80 | 0.06 |
| TALC | 3.35 |
| TRIETHYL CITRATE | 2.50 |
| THEORETICAL CONTENT | 581.2 mg/g |

DV* = dry varnish or dry extract (which remains after evaporation of the solvents).

C) Premounting of Batch YED 005×1406 a) Preparation of the Premounting Suspension

Refer to paragraph II D) a) of Example 5.2.

b) Premounting of the Diltiazem Microgranules

The microgranules to be premounted are placed in a coating turbomixer,

The microgranules are premounted at a temperature of 30° C. by continuous spraying of the suspension described above, The mass of microgranules obtained is screened through a grille with a mesh size of 1.50 mm, The microgranules are then dried in a rotating turbomixer at a temperature of 35° C. for 2 h.

c) Formulation of Batch YED 005×1406 after Premounting

| Composition of the DV* | Amount in % |
|---|---|
| DILTIAZEM | 52.36 |
| NEUTRAL 30 | 14.98 |
| PVP K 17 | 1.40 |
| SODIUM LAURYL SULPHATE | 0.70 |
| DIETHYL PHTHALATE | 0.70 |
| EUDRAGIT RS 30 D | 14.06 |
| EUDRAGIT L 30 D | 9.01 |
| DIBUTYL SEBACATE | 0.56 |
| POLYSORBATE 80 | 0.06 |
| TALC | 3.02 |
| TRIETHYL CITRATE | 3.16 |
| THEORETICAL CONTENT | 523.6 mg/g |

DV* = dry varnish or dry extract (which remains after evaporation of the solvents).

D) Mounting of the Second Layer of Diltiazem on Batch YED 005×1406 a) Preparation of the Mounting Solution

Refer to paragraph A) a) of Example 5.1.

b) Mounting of the Diltiazem

The active principle is mounted on microgranules obtained from the protective coating of batch YED 005×1406, by discontinuous spraying of the suspension described above, in alternance with sequences of dusting of the Diltiazem and sequences of leaving to stand, The mass of microgranules obtained is screened through a grille with a mesh size of 1.60 to 1.80 mm, The microgranules are then dried in the rotating turbomixer at room temperature for 12 h.

c) Formulation of Batch YED 005×1406 after Mounting of the Second Layer of Diltiazem

| Composition of the DV* | Amount in % |
|---|---|
| DILTIAZEM | 62.58 |
| NEUTRAL 30 | 11.08 |
| PVP K 17 | 2.13 |
| SODIUM LAURYL SULPHATE | 1.06 |
| DIETHYL PHTHALATE | 1.06 |
| EUDRAGIT RS 30 D | 10.40 |
| EUDRAGIT L 30 D | 6.66 |
| DIBUTYL SEBACATE | 0.41 |
| POLYSORBATE 80 | 0.04 |
| TALC | 2.23 |
| TRIETHYL CITRATE | 2.33 |
| THEORETICAL CONTENT | 625.8 mg/g |

DV* = dry varnish or dry extract (which remains after evaporation of the solvents).

E) External Coating of Batch YED 005×1406 a) Preparation of the Coating Suspension

Refer to paragraph I B) a) of Example 5.2.

b) External Coating of the Diltiazem Microgranules

The microgranules to be coated are placed in a coating turbomixer,

The microgranules are coated by continuous spraying of the suspension described above, The mass of microgranules obtained is screened through a grille with a mesh size of 1.50 mm, The microgranules are then dried in a rotating turbomixer at a temperature of 40° C. for 1 h and then at room temperature for 7 h.

c) Formulation of Batch YED 005×1406 after External Coating

| Composition of the DV* | Amount in % |
|---|---|
| DILTIAZEM | 55.46 |
| NEUTRAL 30 | 9.82 |
| PVP K 17 | 1.88 |
| SODIUM LAURYL SULPHATE | 0.94 |
| DIETHYL PHTHALATE | 0.94 |
| EUDRAGIT RS 30 D | 16.30 |
| EUDRAGIT L 30 D | 5.91 |
| DIBUTYL SEBACATE | 0.65 |
| POLYSORBATE 80 | 0.07 |
| TALC | 4.82 |
| TRIETHYL CITRATE | 3.20 |
| THEORETICAL CONTENT | 554.6 mg/g |

DV* = dry varnish or dry extract (which remains after evaporation of the solvents).

F) Results of Dissolution after Internal Coating and External Coating (in Two Media)

| | YED 005 × 1406 Internal coating (in %) | YED 005 × 1406 premounting (in %) H₂O | YED 005 × 1406 External coating (in %) | YED 005 × 1406 Premounting (in %) | YED 005 × 1406 Mounting of the second layer of Diltiazem (in %) pH 7 | YED 005 × 1406 External coating (in %) |
|---|---|---|---|---|---|---|
| 1 h | 0.08 | 0.35 | 7.35 | 0.40 | 39.51 | 16.72 |
| 2 h | 0.35 | 0.46 | 32.78 | 0.66 | 39.67 | 31.36 |
| 3 h | 0.53 | 0.51 | 36.32 | 0.81 | 39.76 | 32.44 |
| 4 h | 0.70 | 0.55 | 37.09 | 1.01 | 39.85 | 32.61 |
| 5 h | 1.20 | 0.61 | 37.39 | 1.21 | 39.93 | 32.84 |
| 6 h | 2.53 | 0.66 | 37.76 | 1.61 | 40.15 | 33.13 |
| 7 h | 5.96 | 0.70 | 38.06 | 2.42 | 40.45 | 33.36 |
| 8 h | 15.30 | 0.81 | 38.17 | 6.81 | 40.77 | 33.93 |
| 9 h | 38.46 | 1.06 | 36.41 | 21.45 | 41.83 | 34.64 |
| 10 h | 67.09 | 1.91 | 36.72 | 39.58 | 44.51 | 36.50 |

-continued

F) Results of dissolution after internal coating and external coating (in two media)

|  | YED 005 × 1406 Internal coating (in %) | YED 005 × 1406 External premounting (in %) H₂O | YED 005 × 1406 External coating (in %) | YED 005 × 1406 Premounting (in %) | YED 005 × 1406 Mounting of the second layer of Diltiazem (in %) pH 7 | YED 005 × 1406 External coating (in %) |
|---|---|---|---|---|---|---|
| 11 h | 84.19 | 5.19 | 39.04 | 51.16 | 50.59 | 39.63 |
| 12 h | 91.67 | 13.24 | 39.63 | 57.65 | 62.44 | 44.44 |
| 13 h | 95.19 | 22.93 | 40.53 | 62.19 | 75.44 | 50.52 |
| 14 h | 97.22 | 30.22 | 41.72 | 65.61 | 83.95 | 56.66 |
| 15 h | 98.59 | 35.49 | 43.21 | 68.12 | 87.96 | 62.41 |
| 16 h | 99.99 | 35.96 | 44.99 | 70.28 | 89.97 | 67.04 |
| 17 h | 100.84 | 42.77 | 46.91 | 71.89 | 90.94 | 70.91 |
| 18 h | 101.59 | 45.36 | 49.49 | 73.18 | 91.69 | 74.04 |
| 19 h | 102.34 | 47.84 | 52.20 | 74.75 | 92.29 | 76.36 |
| 20 h | 102.89 | 50.05 | 55.51 | 75.80 | 92.95 | 78.34 |
| 21 h | 103.34 | 51.88 | 58.72 | 76.84 | 93.40 | 79.91 |
| 22 h | 103.81 | 53.78 | 62.01 | 77.69 | 93.78 | 81.11 |
| 23 h | 104.29 | 55.59 | 65.15 | 78.70 | 94.14 | 82.28 |
| 24 h | 104.69 | 57.19 | 68.06 | 79.50 | 94.37 | 83.04 |

Percentage of Diltiazem dissolved at each hour of sampling

G) Formulations of Batch YED 005×1406 percentages given on a weight basis for a total of 100 (excluding coating):

|  | YED 005 × 1406 |
|---|---|
| Mounting | |
| Active principle | 80.32% |
| Neutral support | 14.22% |
| Binder | 2.73% |
| Surfactant | 1.36% |
| Plasticizer | 1.36% | percentage on a dry weight basis for a total of 100% (final composition):

|  | YED 005 × 1406 |
|---|---|
| Neutral support | 9.82% |
| Mounting | |
| Active principle | 55.46% |
| Binder | 1.88% |
| Surfactant | 0.94% |
| Plasticizer | 0.94% |
| Coating | |
| Coating agent | 22.21% |
| Bioavailability adjuvant | 0.07% |
| Plasticizer | 3.85% |
| Lubricant | 4.82% |

What is claimed is:

1. Sustained-release (SR) microgranules containing Diltiazem which are free from water-soluble organic acid, comprising,
   a neutral granular support coated with an active layer comprising:
      Diltiazem or a pharmaceutically acceptable salt thereof as active principle,
      a surfactant, and
      a binder,
   a layer which ensures slow sustained release of the active principle (SR layer), and
   another active layer coating the SR layer, comprising:
      Diltiazem or a pharmaceutically acceptable salt thereof as active principle,
      a surfactant, and
      a binder,
   which is itself coated with an external layer which ensures rapid sustained release of the active principle contained in said another layer coating the SR layer.

2. Microgranules according to claim 1, characterized in that they have the following final composition, the percentages being expressed on a dry weight basis for a total of 100%:

| neutral granular support | 20–25% |
|---|---|
| active layer: | |
| active principle | 45–65% |
| binder | 0.5–2% |
| surfactant | 0.5–1% |
| plasticizer | 0.5–1% |
| SR layer: | |
| coating agent | 10–30% |
| bioavailability adjuvant | 0.05–0.15% |
| plasticizer | 2–10% |
| lubricant | 2–10%. |

3. Microgranules according to claim 1, characterized in that the SR layer ensures rapid sustained release of the active principle.

4. Microgranules according to claim 1, characterized in that they have the following final composition, the percentages being expressed on a dry weight basis for a total of 100%:

| | |
|---|---|
| neutral granular support active layers: | 5–15% |
| active principle | 45–65% |
| binder | 0.5–2.5% |
| surfactant | 0.75–1.25% |
| plasticizer | 0.75–1.25% |

| | |
|---|---|
| SR layers: | |
| coating agent | 15–35% |
| bioavailability adjuvant | 0.02–0.15% |
| plasticizer | 2–10% |
| lubricant | 2–10%. |

5. Microgranules according to claim 1, characterized in that they also comprise an intercalating layer between the SR layer which ensures slow release of the active principle and the active layer coating this SR layer.

6. Microgranules according to claim 1, characterized in that the surfactant is an anionic, nonionic, cationic or amphoteric surfactant.

7. Microgranules according to claim 6, characterized in that the surfactant is an anionic surfactant.

8. Microgranules according to claim 1, characterized in that the binder consists of any pharmaceutically acceptable binder which is useful for coating neutral granular supports.

9. Microgranules according to claim 1, characterized in that each active layer also comprises a plasticizer.

10. Microgranules according to claim 1, characterized in that the active principle/surfactant weight ratio is between 99/1 and 95/5.

11. Microgranules according to claim 1, characterized in that the active principle/binder weight ratio is between 99/1 and 90/10.

12. Microgranules according to claim 1, characterized in that they comprise the following components for the support and the active layer, the percentages being given on a weight basis for a total of 100:

| | |
|---|---|
| neutral granular support | 20–25% |
| active principle | 70–75% |
| surfactant | 0.5–5% |
| binder | 0.5–10% |
| plasticizer | 0–5%. |

13. Microgranules according to claim 1, characterized in that they comprise the following components for the support and the active layers, the percentages being given on a weight basis for a total of 100:

| | |
|---|---|
| neutral granular support | 10–20% |
| active principle | 75–85% |
| surfactant | 0.5–5% |
| binder | 0.5–10% |
| plasticizer | 0.5–5%. |

14. Microgranules according to claim 1, characterized in that each SR layer consists of a coating agent which ensures sustained release, optionally combined with one or more common additives.

15. Microgranules according to claim 14, wherein said one or more common additives are selected from the group consisting of a bioavailability adjuvant, a plasticizer, and a lubricant.

16. Microgranules according to claim 15, characterized in that the bioavailability adjuvant is a fatty acid ester of polyoxyethylene.

17. Microgranules according to claim 14, characterized in that the lubricant is talc.

18. Microgranules according to claim 15, characterized in that the plasticizer is a pharmaceutically acceptable common plasticizer used for the preparation of microgranules.

19. Microgranules according to claim 16, wherein said fatty acid ester of polyoxyethylene is described under the name Polysorbate.

20. Microgranules according to claim 18, wherein said pharmaceutically acceptable common plasticizer comprises an ester of a citric acid, a phthalic acid, or a sebacic acid, or a mixture thereof.

21. Gelatin capsules comprising microgranules according to claim 1.

22. Microgranules according to claim 1, characterized in that they have the following final composition, the percentage being expressed on a dry weight basis for a total of 100%:

| | |
|---|---|
| neutral granular support active layers: | 5–15% |
| active principle | 45–65% |
| binder | 0.5–2% |
| surfactant | 0.5–1% |
| plasticizer | 0.5–1% |

| | |
|---|---|
| SR layers: | |
| coating agent | 10–30% |
| bioavailability adjuvant | 0.02–0.15% |
| plasticizer | 2–10% |
| lubricant | 2–10%. |

23. Microgranules according to claim 7, wherein said anionic surfactant is an alkali metal ($C_{10}$–$C_{20}$) alkyl sulphate.

24. Microgranules according to claim 23, wherein said alkali metal ($C_{10}$–$C_{20}$) alkyl sulphate is selected from the group consisting of sodium lauryl sulphate, an alkali metal ($C_{10}$–$C_{20}$) sulphonate or an alkali metal ($C_{10}$–$C_{20}$) alkyl benzenesulphonate.

25. Microgranules according to claim 8, wherein said binder consists of a pharmaceutically acceptable polymer.

26. Microgranules according to claim 25, wherein said pharmaceutically acceptable polymer is a polyvinylpyrrolidone.

27. Microgranules according to claim 9, wherein said plasticizer is a phthalic acid ester.

28. Microgranules according to claim 10, wherein said active principle/surfactant weight ratio is about 98/2.

29. Microgranules according to claim 11, wherein said active principle/binder weight ratio is about 97/3.

30. Microgranules according to claim 14, characterized in that the coating agent ensuring the sustained release is a water-insoluble film-forming polymer.

31. Microgranules according to claim 30, wherein said waterinsoluble film-forming polymer is a polymethacrylate.

32. Microgranules according to claim 20, wherein said citric acid is triethyl citrate.

33. Microgranules according to claim 20, wherein said phthalic acid ester is diethyl phthalate.

34. Microgranules according to claim 20, wherein said sebacic acid ester is dibutyl sebacate.

* * * * *